US009510774B2

(12) United States Patent
Russell

(10) Patent No.: US 9,510,774 B2
(45) Date of Patent: Dec. 6, 2016

(54) GAS MEASUREMENT MODULE FOR USE IN THERAPEUTIC SETTINGS COMPRISING REFLECTIVE SCANNING MICROSPECTROMETER

(75) Inventor: James Torrance Russell, Bellevue, WA (US)

(73) Assignee: Koninklijke Philips N.V., Eindhoven (NL)

( * ) Notice: Subject to any disclaimer, the term of this patent is extended or adjusted under 35 U.S.C. 154(b) by 861 days.

(21) Appl. No.: 13/514,476

(22) PCT Filed: Dec. 1, 2010

(86) PCT No.: PCT/IB2010/055535
§ 371 (c)(1),
(2), (4) Date: Jun. 7, 2012

(87) PCT Pub. No.: WO2011/070485
PCT Pub. Date: Jun. 16, 2011

(65) Prior Publication Data
US 2012/0242980 A1    Sep. 27, 2012

Related U.S. Application Data

(60) Provisional application No. 61/267,929, filed on Dec. 9, 2009.

(51) Int. Cl.
| | |
|---|---|
| *G01J 5/10* | (2006.01) |
| *A61B 5/08* | (2006.01) |
| *G01N 21/3504* | (2014.01) |
| *G01N 33/497* | (2006.01) |
| *G01J 5/20* | (2006.01) |
| *G01N 21/3563* | (2014.01) |

(Continued)

(52) U.S. Cl.
CPC ............... *A61B 5/08* (2013.01); *A61B 5/082* (2013.01); *G01N 21/3504* (2013.01); *G01N 33/497* (2013.01); *G01J 5/02* (2013.01); *G01J 5/10* (2013.01); *G01J 5/20* (2013.01); *G01N 21/3563* (2013.01); *G01N 21/3581* (2013.01)

(58) Field of Classification Search
USPC ............................................. 250/338.1, 353
See application file for complete search history.

(56) References Cited

U.S. PATENT DOCUMENTS 3,792,272 A * 2/1974 Harte et al. ............... 250/343
3,848,974 A * 11/1974 Hosking et al. ............ 345/7
3,924,925 A * 12/1975 Gale et al. .................. 359/24

(Continued)

OTHER PUBLICATIONS

Collimated Light [online], [retrieved on May 17, 2015]. Retrieved from the Internet:<URL:http://en.wikipedia.org/wiki/Collimated_light>.*

*Primary Examiner* — Christine Sung

(57) ABSTRACT

Gas within a ventilation circuit is analyzed by a spectrometer included in an airway adaptor that is inserted into the ventilation circuit. The spectrometer is formed from reflective members that process electromagnetic radiation while folding the path of the electromagnetic radiation in such a manner that the form factor of the airway adaptor is enhanced. Further, because of the scale of the spectrometer within the airway adaptor, the cost savings associated with manufacture of the reflective elements instead of refractive elements may significantly reduce the cost of the airway adaptor.

15 Claims, 4 Drawing Sheets

(51) Int. Cl.
*G01J 5/02* (2006.01)
*G01N 21/3581* (2014.01)

(56) References Cited

U.S. PATENT DOCUMENTS

| | | | | |
|---|---|---|---|---|
| 4,225,923 | A | * | 9/1980 | Bloemendaal et al. ...... 362/301 |
| 4,537,508 | A | * | 8/1985 | Doyle ........................... 356/452 |
| 5,070,246 | A | * | 12/1991 | Durham et al. .............. 250/373 |
| 5,369,277 | A | | 11/1994 | Knodle |
| 5,401,966 | A | * | 3/1995 | Gray et al. ................... 250/343 |
| 5,450,193 | A | * | 9/1995 | Carlsen et al. ............... 356/301 |
| 5,534,066 | A | | 7/1996 | O'Neill et al. |
| 5,801,826 | A | | 9/1998 | Williams |
| 6,534,769 | B1 | * | 3/2003 | Graham ........................ 250/343 |
| 7,157,711 | B1 | | 1/2007 | Russell |
| 7,605,370 | B2 | | 10/2009 | Russell |
| 2006/0263916 | A1 | * | 11/2006 | Arno .............................. 438/14 |
| 2007/0164221 | A1 | * | 7/2007 | Russell .................... G01J 3/02 250/339.07 |
| 2010/0002234 | A1 | * | 1/2010 | Cormier et al. ............. 356/436 |

\* cited by examiner

GAS MEASUREMENT MODULE FOR USE IN THERAPEUTIC SETTINGS COMPRISING REFLECTIVE SCANNING MICROSPECTROMETER

BACKGROUND OF THE INVENTION

1. Field of the Invention

The invention relates to an gas measurement module that is insertable into a ventilation circuit, and carries a microspectrometer configured to detect gas composition within the ventilation circuit.

2. Description of the Related Art

Gas analyzers are widely used in medical applications and may be characterized as being located either in the main path of the patient's respiratory gases (mainstream analyzers) or in an ancillary path usually paralleling the main path (sidestream analyzers). A mainstream analyzer is situated such that the subject's inspired and expired respiratory gases pass through an airway adapter onto which the analyzer is placed. A sidestream gas analyzer is coupled to an airway adapter to draw air off from the main respiratory circuit for measurement. Mainstream and sidestream designs for inclusion in gas measurement modules that can be coupled to a respiratory circuit in a therapeutic setting to measure gas composition must be designed to facilitate installation of the gas measurement modules at a patient's airway or in a respiratory circuit in communication with a patient in a location in relatively close proximity to the patient. As a result, to be accepted in therapeutic settings, the gas analyzer must be designed such that the gas measurement module housing the gas analyzer has a convenient and comfortable form factor and/or weight. Further, the gas analyzer must be robust enough to be substantially unaffected by typical mechanical abuse and temperature variations associated with use in therapeutic settings.

While gas measurement modules with gas analyzers employing scanning spectrometers are known, the optics typically employed in these systems to process electromagnetic radiation generally form an optical path having a shape that adversely impacts the overall form factor of the spectrometer, and the gas measurement module as a whole. This impact may be due to one or both of the bulk of the optics and/or the optical path length and orientations dictated to process the electromagnetic radiation appropriately. Further, attempting to reduce the size of the optics and/or enhance the optical path lengths and orientations required to by conventional optics may result in the design of optical configurations that are not robust enough to withstand therapeutic settings and/or optical components that are prohibitively expensive.

SUMMARY OF THE INVENTION

One aspect of the invention relates to a gas measurement module configured to be inserted into a ventilation circuit that is in fluid communication with an airway of a subject. In one embodiment, the gas measurement module comprises a chamber, an infrared source, a collimating reflective optical element, a diffractive reflective optical element, and a photosensitive detector. The chamber has a first opening and a second opening, and is configured to form a flow path between the first opening and the second opening such that if the gas measurement module is inserted into the ventilation circuit, gas from the airway of the subject is transported through the flow path. The infrared source is configured to emit infrared electromagnetic radiation. The collimating reflective optical element is configured to receive infrared electromagnetic radiation emitted by the infrared source, to collimate or substantially collimate the received infrared electromagnetic radiation, and to direct the collimated or substantially collimated infrared electromagnetic radiation along an optical path that passes through the flow path formed by the chamber. The diffractive reflective optical element configured to receive collimated or substantially collimated infrared electromagnetic radiation along the optical path, and to diffract the received collimated or substantially collimated infrared electromagnetic radiation. The photosensitive detector is configured to receive diffracted infrared electromagnetic radiation that has passed through the flow path formed by the chamber from the diffractive reflective optical element, and to generate output signals that convey information related to one or more parameters of the received infrared electromagnetic radiation.

Another aspect of the invention relates to a method of analyzing gas within an gas measurement module configured to be inserted into a ventilation circuit that is in fluid communication with an airway of a subject. In one embodiment, the method comprises generating infrared electromagnetic radiation; reflectively collimating or substantially collimating the generated infrared electromagnetic radiation; directing the collimated or substantially collimated infrared electromagnetic radiation along an optical path that passes through a flow path formed by the gas measurement module within which gas from the airway of the subject flows; reflectively diffracting the collimated or substantially collimated infrared electromagnetic radiation; and generating output signals that convey information related to one or more parameters of the infrared electromagnetic radiation that has been diffracted and has passed through the flow path.

Yet another aspect of the invention relates to a system configured to analyze gas, the system configured to be inserted into a ventilation circuit that is in fluid communication with an airway of a subject. In one embodiment, the system comprises means for generating infrared electromagnetic radiation; means for reflectively collimating or substantially collimating the generated infrared electromagnetic radiation; means for directing the collimated or substantially collimated infrared electromagnetic radiation along an optical path that passes through a flow path formed by the system within which gas from the airway of the subject flows; means for reflectively diffracting the collimated or substantially collimated infrared electromagnetic radiation; and means for generating output signals that convey information related to one or more parameters of the infrared electromagnetic radiation that has been diffracted and has passed through the flow path.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
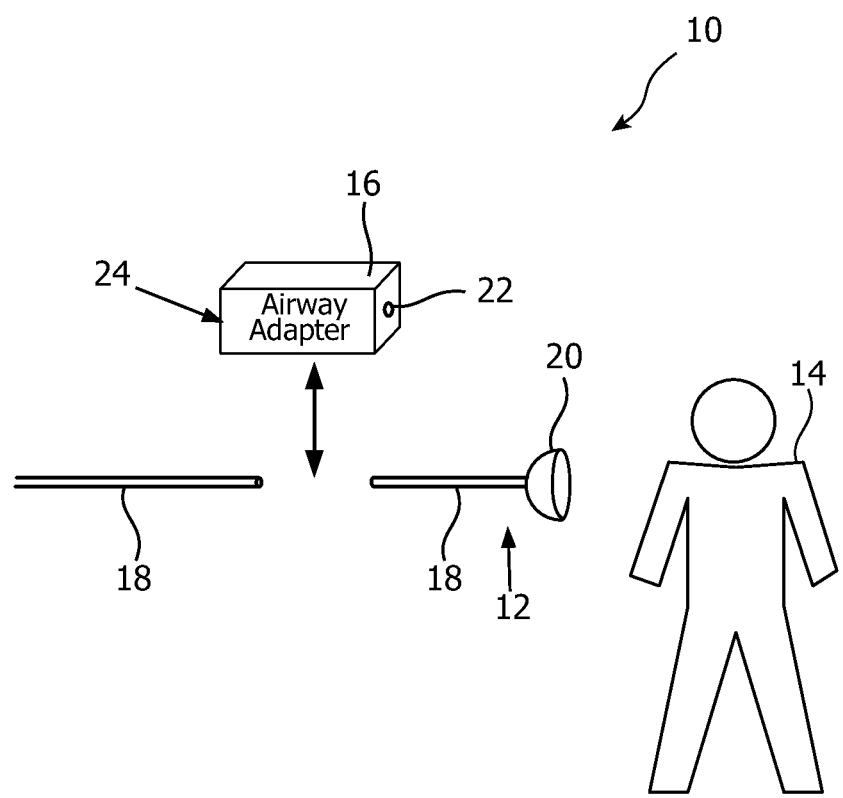
FIG. 1 illustrates a system configured to analyze the composition of gas within a ventilation circuit, according to one or more embodiments of the invention.

FIG. 1 illustrates a system 10 configured to analyze the composition of gas within a ventilation circuit 12 from which a subject 14 may receive ventilation therapy. In one embodiment, the ventilation circuit 12 is connected at one end to a pressure generator configured to generate a pressurized flow of breathable gas for delivery to the airway of subject 14 through ventilation circuit 12. However, this is not intended to be limiting. In one embodiment, system 10 includes an gas measurement module 16.

The ventilation circuit 12 includes a circuit conduit 18 and a subject interface appliance 20. In a number of different therapeutic scenarios, an airway of subject 14 is engaged to place ventilation circuit 12 in fluid communication with the airway of subject 14. The airway of subject 14 is engaged, and placed in fluid communication with ventilation circuit 12, by subject interface appliance 20. The subject interface appliance 20 may engage one or more orifices of the airway of subject 14 in a sealed or unsealed manner. Some examples of subject interface appliance 20 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The circuit conduit 18 is configured to convey gas toward and away from subject interface appliance 20. By way of non-limiting example, circuit conduit 18 may include a flexible conduit. For the purposes of this disclosure, circuit conduit 18 is not necessarily limited to a tubular member that conveys pressurized gas flows to and/or from subject interface appliance 20. The circuit conduit 18 may include any hollow body, container, and/or chamber placed in fluid communication with the airway of subject 14 by subject interface appliance 20. For example, the circuit conduit 18 referred to herein may be formed as a chamber located on the actual subject interface appliance 20. This chamber may be in fluid communication with a gas source, and/or with ambient atmosphere.

The gas measurement module 16 is configured to analyze the composition of gas within ventilation circuit 12. As such, gas measurement module 16 is configured to be placed in communication with circuit conduit 18. This may include insertion of gas measurement module 16 into circuit conduit 18. This insertion may be selectively removable, and/or substantially permanent. In one embodiment, ventilation circuit 12 includes a dock in circuit conduit 18 configured to removably receive gas measurement module 16 therein. The gas measurement module 16 forms a chamber therein having a first opening 22 and a second opening 24 disposed on gas measurement module 16 such that if gas measurement module 16 is inserted into circuit conduit 18, gas is transported to and/or from the airway of subject 14 through a flow path between first opening 22 and second opening 24 formed by the chamber. In some implementations, the chamber is formed as a sidestream chamber (rather than a mainstream chamber). In these implementations, gas passing through gas measurement module 16 between first opening and second opening 24 is drawn off into the sidestream chamber for analysis.

The gas measurement module 16 carries optical and/or electronic components that facilitate analysis of the composition of the gas within the chamber formed by gas measurement module 16. These components may form, for instance, a diffraction grating spectrometer. In order to facilitate the use of gas measurement module 16 in therapeutic settings, the optical and/or electronic components of gas measurement module 16 that facilitate composition analysis are configured to minimize the form factor of gas measurement module 16. For example, if gas measurement module 16 is too bulky and/or awkward, then implementation may be difficult (e.g., susceptible to inadvertent disconnection and/or breakage), uncomfortable for subject 14, and/or have other draw backs.

Figure 2:
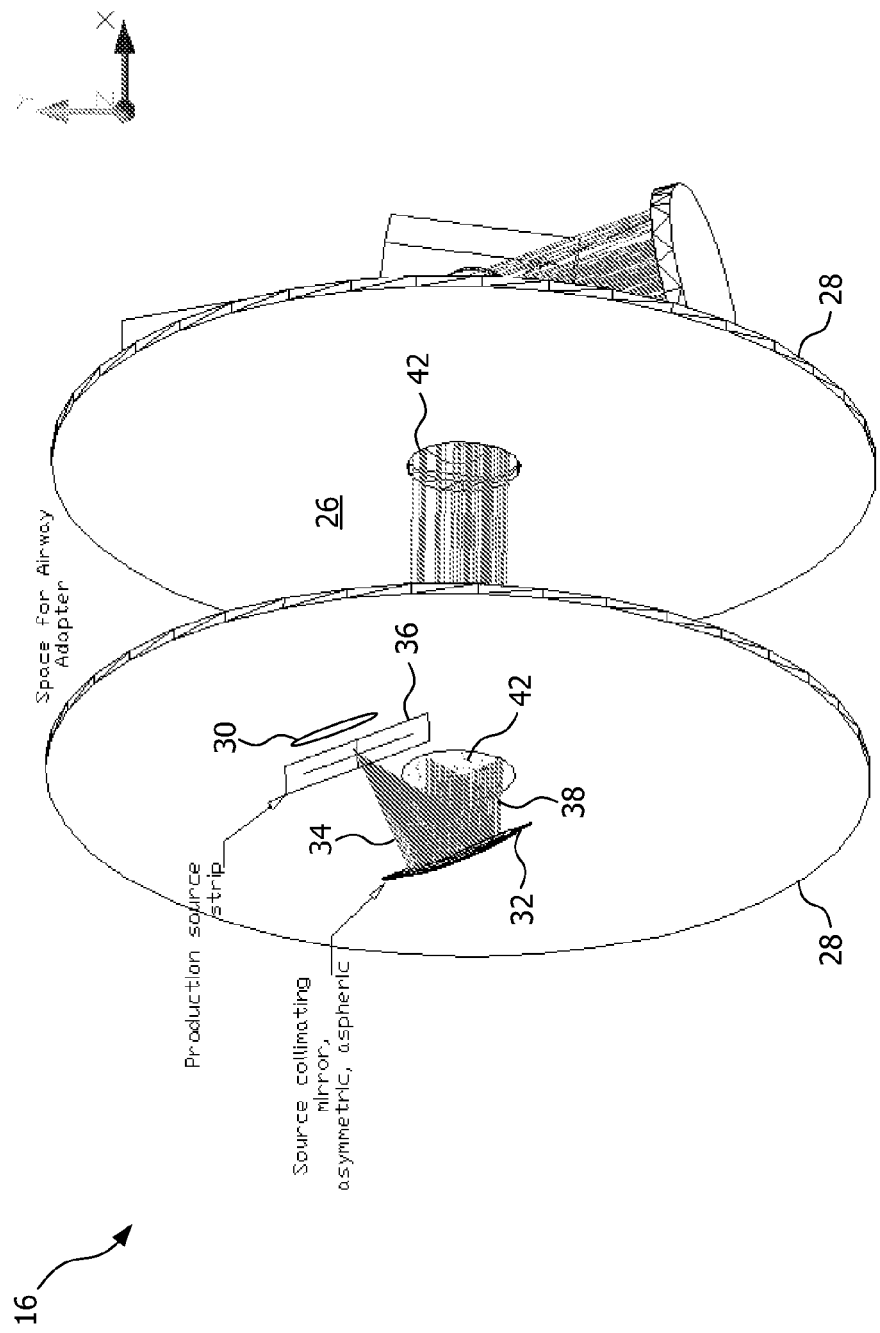
FIG. 2 illustrates components of a spectrometer included in an gas measurement module, in accordance with one or more embodiments of the invention.

FIG. 2 illustrates an exemplary configuration of components of gas measurement module 16 that enable composition analysis of gas within gas measurement module 16. In FIG. 2, the chamber formed by gas measurement module 16 is identified as element 26 bounded by walls 28. It will be appreciated that the illustration of chamber 26 as only being formed by walls 28 is to enable the components of gas measurement module 16 that analyze gaseous composition to be viewed more easily. Further, the illustration of chamber 26 as being bounded by flat, parallel walls 28 is also illustrative. For example, chamber 26 may be formed having a round cross-section and/or a cross-section of some other shape.

In the view of gas measurement module 16 shown in FIG. 2, a source 30 and a collimating reflective optical element 32 can be seen positioned to one side of the walls 28 that form chamber 26. The source 30 is configured to emit electromagnetic radiation 34 in the infrared spectrum. In one embodiment, the electromagnetic radiation 34 includes electromagnetic radiation in a first wavelength band related to carbon dioxide and nitrous oxide (e.g., between about 3.5 and about 5 microns) and/or a second wavelength band related to one or more anesthetic agents.

In one embodiment, in the optical system formed within gas measurement module 16 includes a slit 36 disposed between source 30 and collimating reflective optical element 32. In this embodiment, the optical system images slit 36 as the source of the electromagnetic radiation. This may enhance resolution of the "source" in the system caused by magnification during processing of the electromagnetic radiation.

The collimating reflective optical element 32 is configured to collimate electromagnetic radiation 34 to produce a collimated beam of electromagnetic radiation 38 that is directed along an optical path that traverses the flow path formed within chamber 26. As can be seen in FIG. 2, collimating reflective optical element 32 is formed such that source 30 can be disposed off of the optical axis of electromagnetic radiation 38, and even off of the optical path of electromagnetic radiation 38. This provides enhancements in form factor over conventional source/reflector configurations in which the source is in the optical path (if not on the optical axis) of collimated light reflected from the collimating reflector.

As should be appreciated, in gas measurement module 16 if a conventional source/reflector configuration were used to collimate electromagnetic radiation 38, the distance between collimating reflective optical element 32 and walls 28 would be increased by the bulk of source 30 and the distance required for the electromagnetic radiation 34 to disperse from source 30 to an appropriate cross-sectional size for beam of electromagnetic radiation 38. This increased distance requirement would be reflected in the overall form factor of gas measurement module 16 and would manifest itself in an increased width of gas measurement module 16. By contrast, with the source 30 positioned out of the optical path of electromagnetic radiation 38 the volume of gas measurement module 16 associated with the bulk of source 30 and the distance required for dispersal of electromagnetic radiation 34 can be positioned to run with the length and/or the height of gas measurement module 16, and not significantly impact the width of gas measurement module 16.

The collimating reflective optical element 32 may provide enhancements over systems that require refractive elements for collimation. gas measurement module 16 In the wavelength range(s)s to be processed by collimating reflective optical element 32 (e.g., infrared), materials for refractive optical elements are somewhat limited (e.g., silicon, salts). These materials tend to be expensive and hard to work with. Particularly on the size scale to be used in gas measurement module 16. Further, these refractive materials tend to take up a relatively large amount of space. On the other hand refractive optical elements may provide for a larger field of view than collimating reflective optical element 32. However, the advantages to be gained in cost, size, and ease of manufacture turn out to vastly outweigh this relative disadvantage in the use of a reflective element to collimate electromagnetic radiation 34. Particularly with respect to the microspectrometer design discussed herein, for which the field of view provided by collimating reflective optical element 32 is sufficient. gas measurement module 16 gas measurement module 16

Figure 3:
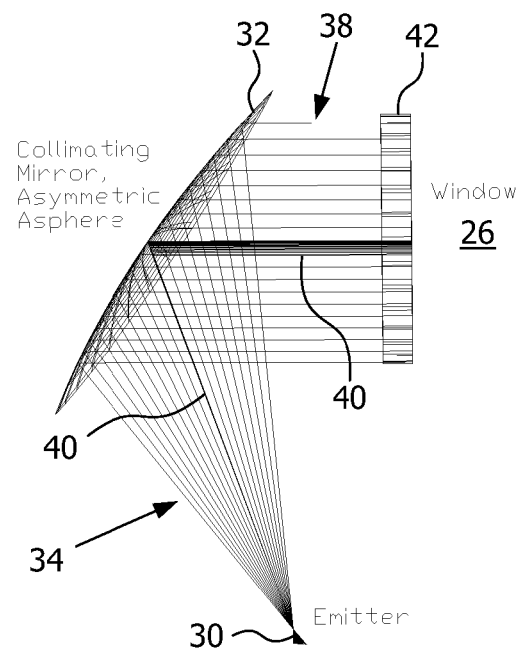
FIG. 3 illustrates components of a spectrometer included in an gas measurement module, in accordance with one or more embodiments of the invention.

FIG. 3 illustrates a ray-tracing that shows the manner in which electromagnetic radiation 34 emitted by source 30 is collimated and folded by collimating reflective optical element 32. In the embodiment shown in FIG. 3, collimating reflective optical element 32 has a reflective surface that is asymmetric and aspherical. For example, the reflective surface may be a parabolic shaped reflector formed from an off-axis parabolic section. FIG. 3 further shows how source 30 is disposed off of the optical path of electromagnetic radiation 38. Because of the positioning of source 30 to reduce the width of gas measurement module 16, as was discussed above, a central ray 40 of electromagnetic radiation 34 becomes incident on collimating reflective optical element 32 along a path that has an acute angle with respect to the plane of walls 28 where electromagnetic radiation 38 enters chamber 26. In an embodiment in which walls 28 are rounded, this plane would be the plane tangential to wall 28 where central ray 40 enters chamber 26. For example, this angle θ may be less than 45 degrees In one embodiment, collimating reflective optical element 32 is formed from molded plastic, and/or other materials. The reflective surface of collimating reflective optical element 32 may be formed by gold, aluminum, and/or other reflective materials, and/or other coatings and/or materials. By virtue of the configuration of source 30 and collimating reflective optical element 32 described above, the distance from wall 28 to the outer edge of collimating reflective optical element 32 shown in FIG. 3 as d that must be accommodated by the width of chamber 26 may be less than about 2 mm.

Returning now to FIG. 2, to accommodate electromagnetic radiation 38 passing through chamber 26, walls 28 include a pair of optically transmissive windows 42. The windows 42 may be formed, for example, from silicon, germanium, sapphire, and/or other materials.

Figure 4:
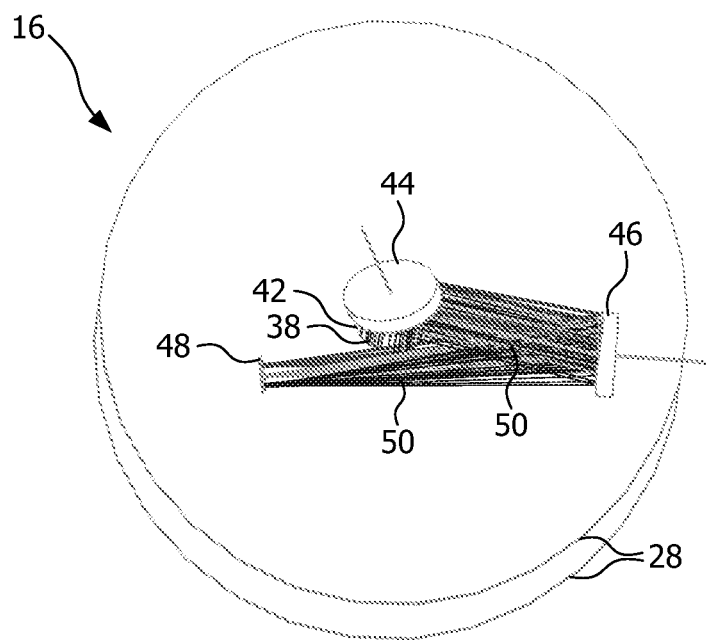
FIG. 4 illustrates components of a spectrometer included in an gas measurement module, in accordance with one or more embodiments of the invention

FIG. 4 shows a view of the components of gas measurement module 16 on the opposite side of gas measurement chamber 26 from the view shown in FIG. 3. Specifically, in the view shown in FIG. 4, a diffractive reflective optical element 44, a focusing reflective optical element 46, and a photosensitive detector 48 are shown.

The diffractive reflective optical element 44 is configured to diffract electromagnetic radiation 38 after electromagnetic radiation 38 has traversed chamber 26. At least a portion of electromagnetic radiation 38 diffracted by diffractive reflective optical element 44 forms a beam of diffracted electromagnetic radiation 50 that becomes incident on focusing reflective optical element 46. The diffraction of electromagnetic radiation at diffractive reflective optical element 44 is effective by diffractive elements formed on the reflective surface of diffractive reflective optical element 44. The diffractive elements may include grating lines. The grating lines may be spaced at about 20 microns, and/or at other wavelength-related spacings. In order to accommodate analysis over the portions of the infrared spectrum required for useful analysis of the composition of gas within chamber 26, diffractive reflective optical element 44 oscillated about an axis of rotation. The axis of rotation is parallel to the diffraction gratings and ideally is in the plane of the gratings. In one embodiment, diffractive reflective optical element 44 is formed from replicated or molded plastic, and/or other materials, with a gold, aluminum, or other reflective material coating providing the reflective surface.

As was discussed above with respect to FIG. 2, slit 36 may be arranged between source 30 and collimating reflective optical element 32 to improve resolution within gas measurement module 16. The slit 36 may be oriented in a direction that is substantially parallel to the diffraction gratings formed on diffractive reflective optical element 44 when electromagnetic radiation from slit 36 is projected by gas measurement module 16 reflector 32 onto diffractive reflective optical element 44.

Referring again specifically to FIG. 4, the focusing reflective optical element 46 configured to receive electromagnetic radiation 50 and to focus electromagnetic radiation 50 onto photosensitive detector 48. In one embodiment, focusing reflective optical element 46 is formed from replicated or molded plastic, and/or other materials, with a gold, aluminum, or other reflective material coating providing the reflective surface.

The photosensitive detector 48 is configured to receive the electromagnetic radiation 50 focused by focusing reflective optical element 46, and to generate output signals that convey information related to one or more parameters of the received electromagnetic radiation 50. The one or more parameters may include, for example, intensity as a function of wavelength, and/or other parameters. A slit (not shown) may be disposed at photosensitive detector 48 such that the parameter(s) of electromagnetic radiation 50 detected by photosensitive detector 48 provide an indication of the intensity of a specific wavelength range of electromagnetic radiation 38, which is commensurate with the molecular species being monitored, after electromagnetic radiation 38 has passed through chamber 26.

Since the spectral signature of the gas within chamber 26 will vary with the composition of the gas within chamber 26, detection of intensities of specific wavelengths of electromagnetic radiation 38 after electromagnetic radiation 38 has passed through chamber 26 will enable determinations of the composition of gas within chamber 26. Such determinations may be made by a processor (not shown) configured to receive the output signals generated by photosensitive detector 48. In order to determine the wavelength of electromagnetic radiation 50 incident on photosensitive detector 48 at a given point in time, the processor may be provided with information related to the scanning position and/or frequency of diffractive reflective optical element 44 at a given point in time.

Figure 5:
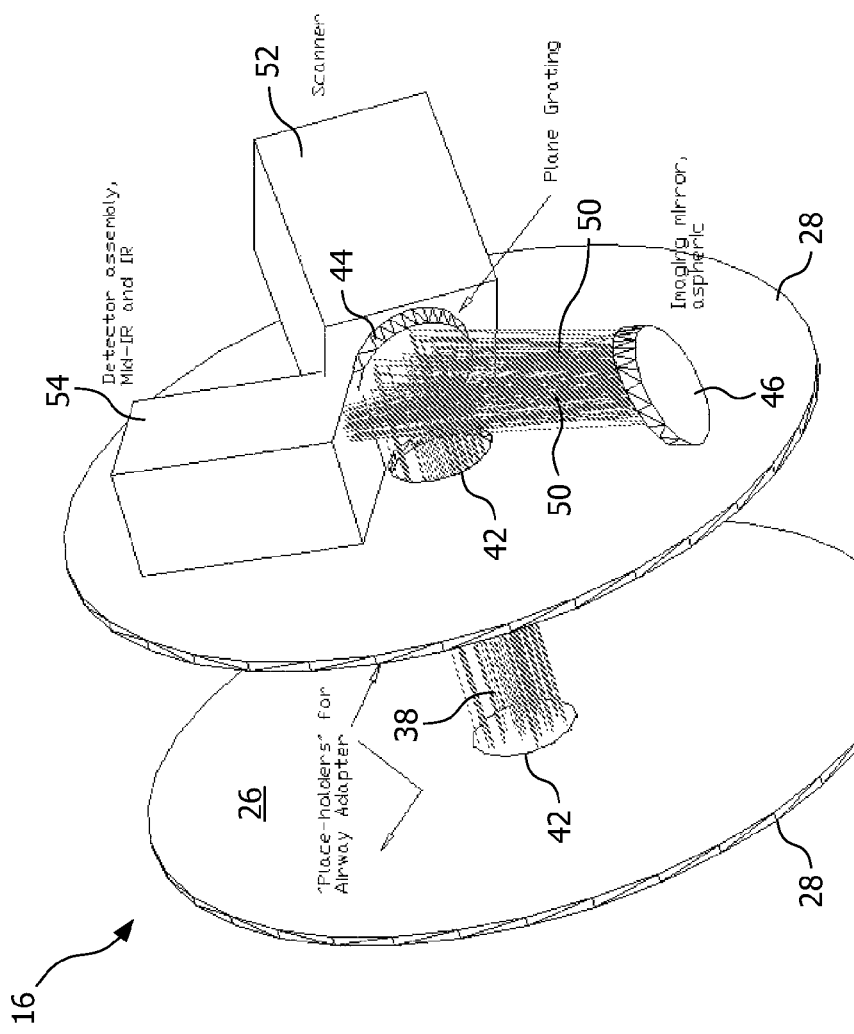
FIG. 5 illustrates components of a spectrometer included in an gas measurement module, in accordance with one or more embodiments of the invention.

FIG. 5 illustrates a view of gas measurement module 16 that shows a scanner module 52 and a detector module 54. The scanner module 52 is configured to oscillate diffractive reflective optical element 44 about its axis of rotation. This oscillation may have a predetermined frequency and/or range. One or more exemplary embodiments of scanner module 52 are described, for example in U.S. Pat. No. 7,605,370, entitled "Microspectrometer Gas Analyzer," issued Oct. 20, 2009, and incorporated into this disclosure in its entirety ("the '370 patent")

The detector module 54 may be configured to detect a plurality of spectral bands of within electromagnetic radiation 50. In order to detect the separate bands, detector module 54 may include one or more beam splitters that divide electromagnetic radiation into a plurality of separate beams, and a plurality of photosensitive detectors configured to receive different spectral bands as diffractive reflective optical element 44 is oscillated over its range. For example, several such configurations of collimating element, diffraction elements, beam splitter(s), focusing element(s), and photosensitive detectors are described in the '370 patent. It will be appreciated that the particular configuration of the optical elements in this disclosure, and in the '370 patent are not intended to be limiting. The scope of this disclosure includes embodiments, by way of non-limiting example, in which diffractive reflective optical element 44 is positioned on the other side of chamber 26. Other potential configurations will also be apparent.

As can be seen in FIG. 5, diffractive reflective optical element 44, focusing reflective optical element 46, and/or detector module 54 may be arranged such that the optical path of electromagnetic radiation 50 between diffractive reflective optical element 44 and detector module 54 is substantially parallel with wall 28 at the location where electromagnetic radiation 38 passes through. This may enable the optical length required to suitably process electromagnetic radiation 50 between diffractive reflective optical element 44 and detector module 54 to be attained within gas measurement module 16 without adding the entire distance to the width of gas measurement module 16. As was discussed above, this may enhance the usability, comfort, and/or other aspects of gas measurement module 16 in a therapeutic setting.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas measurement module configured to be inserted into a ventilation circuit that is in fluid communication with an airway of a subject, the gas measurement module comprising:

a chamber having a first opening and a second opening, wherein the chamber is configured to form a flow path between the first opening and the second opening such that if the gas measurement module is inserted into the ventilation circuit, gas from the airway of the subject is transported through the flow path;

an infrared source configured to emit infrared electromagnetic radiation;

a collimating reflective optical element configured to receive infrared electromagnetic radiation emitted by the infrared source, to collimate or substantially collimate the received infrared electromagnetic radiation, and to direct the collimated or substantially collimated infrared electromagnetic radiation along an optical path that passes through the flow path formed by the chamber, wherein the collimating reflective optical element has a reflective surface that comprises a parabolic shaped reflector formed from an off-axis parabolic section;

a diffractive reflective optical element configured to receive collimated or substantially collimated infrared electromagnetic radiation along the optical path, and to diffract the received collimated or substantially collimated infrared electromagnetic radiation; and a photosensitive detector configured to receive diffracted infrared electromagnetic radiation that has passed through the flow path formed by the chamber from the diffractive reflective optical element, and to generate output signals that convey information related to one or more parameters of the received infrared electromagnetic radiation.

2. The gas measurement module of claim 1, wherein the collimating reflective optical element is configured to collimate or substantially collimate the received infrared electromagnetic radiation, and to direct the collimated or substantially collimated infrared electromagnetic radiation into the flow path formed by the chamber in a direction that is transverse to the flow path.

3. The gas measurement module of claim 1, wherein the collimating reflective optical element has a reflective surface that is an asymmetrical parabolic section.

4. The gas measurement module of claim 1, further comprising a focusing reflective optical element configured to receive diffracted infrared electromagnetic radiation from the diffractive reflective optical element, and to focus the diffracted infrared electromagnetic radiation on the photosensitive detector.

5. The gas measurement module of claim 1, further comprising a scanner configured to oscillate the diffractive reflective optical element about an axis of rotation.

6. A method of analyzing gas within a gas measurement module configured to be inserted into a ventilation circuit that is in fluid communication with an airway of a subject, the method comprising:
generating infrared electromagnetic radiation;
reflectively collimating or substantially collimating the generated infrared electromagnetic radiation via a collimating reflective optical element having a reflective surface that comprises a parabolic shaped reflector formed from an off-axis parabolic section;
directing the collimated or substantially collimated infrared electromagnetic radiation along an optical path that passes through a flow path formed by the gas measurement module within which gas from the airway of the subject flows;
reflectively diffracting the collimated or substantially collimated infrared electromagnetic radiation; and
generating output signals that convey information related to one or more parameters of the infrared electromagnetic radiation that has been diffracted and has passed through the flow path.

7. The method of claim 6, wherein the reflective collimation or substantial collimation of the generated infrared electromagnetic radiation, and the directing of the collimated or substantially collimated infrared electromagnetic radiation along an optical path that passes through the flow path formed by the gas measurement module is performed by a single reflective optical element.

8. The method of claim 7, wherein the single reflective optical element has a reflective surface that is an asymmetrical parabolic section.

9. The method of claim 6, further comprising focusing the diffracted infrared electromagnetic radiation on a photosensitive detector configured to generate the output signals.

10. The method of claim 6, further comprising manipulating a diffractive reflective optical element configured to perform the diffracting such that the diffractive reflective optical element oscillates about an axis of rotation.

11. A system configured to analyze gas, the system configured to be inserted into a ventilation circuit that is in fluid communication with an airway of a subject, the system comprising:
means for generating infrared electromagnetic radiation;
means for reflectively collimating or substantially collimating the generated infrared electromagnetic radiation, wherein the reflectively collimating means has a reflective surface that comprises a parabolic shaped reflector formed from an off-axis parabolic section;
means for directing the collimated or substantially collimated infrared electromagnetic radiation along an optical path that passes through a flow path formed by the system within which gas from the airway of the subject flows;
means for reflectively diffracting the collimated or substantially collimated infrared electromagnetic radiation; and
means for generating output signals that convey information related to one or more parameters of the infrared electromagnetic radiation that has been diffracted and has passed through the flow path.

12. The system of claim 11, wherein the means for reflectively collimating or substantially collimating the generated infrared electromagnetic radiation, and the means for directing the collimated or substantially collimated infrared electromagnetic radiation along an optical path that passes through the flow path formed by the system are a single reflective optical element.

13. The system of claim 12, wherein the single reflective optical element has a reflective surface that is an asymmetrical parabolic section.

14. The system of claim 11, further comprising means for focusing the diffracted infrared electromagnetic radiation on the means for generating the output signals.

15. The system of claim 11, further comprising means for oscillating the means for diffracting about an axis of rotation.

* * * * *